(12) United States Patent
Jesunadh et al.

(10) Patent No.: US 10,822,308 B2
(45) Date of Patent: Nov. 3, 2020

(54) PROCESSES FOR THE PREPARATION OF ELUXADOLINE

(71) Applicant: SUN PHARMACEUTICAL INDUSTRIES LIMITED, Mumbai, Maharashtra (IN)

(72) Inventors: Kdv Jesunadh, East Godavari (IN); Murad Ismail Inamdar, Ahmednagar (IN); Mukesh Kumar Madhra, Karnal (IN)

(73) Assignee: Sun Pharmaceutical Industries Limited, Mumbai (IN)

( * ) Notice: Subject to any disclaimer, the term of this patent is extended or adjusted under 35 U.S.C. 154(b) by 0 days.

(21) Appl. No.: 16/312,401

(22) PCT Filed: Jun. 23, 2017

(86) PCT No.: PCT/IB2017/053772
§ 371 (c)(1),
(2) Date: Dec. 21, 2018

(87) PCT Pub. No.: WO2017/221213
PCT Pub. Date: Dec. 28, 2017

(65) Prior Publication Data
US 2019/0202793 A1    Jul. 4, 2019

(30) Foreign Application Priority Data

Jun. 23, 2016    (IN) .............................. 201611021559

(51) Int. Cl.
*C07D 233/64*    (2006.01)
*A61P 1/12*    (2006.01)

(52) U.S. Cl.
CPC .............. *C07D 233/64* (2013.01); *A61P 1/12* (2018.01)

(58) Field of Classification Search
None
See application file for complete search history.

(56) References Cited

U.S. PATENT DOCUMENTS 7,741,356 B2 * 6/2010 Breslin .............. A61K 31/4174
514/396

* cited by examiner

*Primary Examiner* — Kamal A Saeed

(57) ABSTRACT

The present invention relates to processes for the preparation of eluxadoline and its intermediates.

6 Claims, No Drawings

PROCESSES FOR THE PREPARATION OF ELUXADOLINE

FIELD OF THE INVENTION

The present invention relates to processes for the preparation of eluxadoline and its intermediates.

BACKGROUND OF THE INVENTION

Eluxadoline, chemically 5-[[[(2S)-2-amino-3-[4-(aminocarbonyl)-2,6-dimethylphenyl]-1-oxopropyl][(1S)-1-(4-phenyl-1H-imidazol-2-yl)ethyl]amino]methyl]-2-methoxybenzoic acid, is represented by Formula I.

Formula I

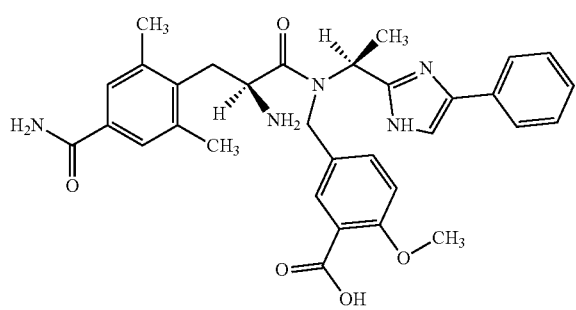

Eluxadoline is a mu-opioid receptor agonist, indicated in adults for the treatment of irritable bowel syndrome with diarrhea (IBS-D).

U.S. Pat. No. 7,741,356 describes a process for the preparation of eluxadoline comprising cyclizing $N^2$-[(benzyloxy)carbonyl]-N-(2-oxo-2-phenylethyl)-L-alaninamide of Formula III Formula III

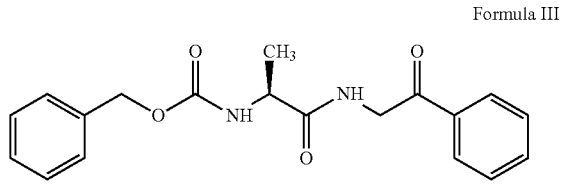 [SMILES: C[C@H](NC(=O)OCc1ccccc1)C(=O)NCC(=O)c1ccccc1]

with ammonium acetate in xylene to obtain benzyl [(1S)-1-(5-phenyl-1H-imidazol-2-yl)ethyl]carbamate of Formula II, which is then purified by column chromatography. The present inventors have observed that when this reaction is performed, an emulsion is formed during work up.

Formula II

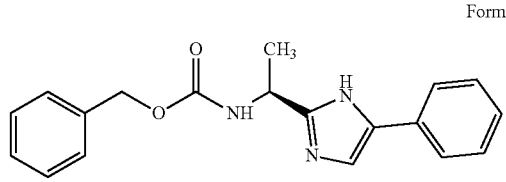

SUMMARY OF THE INVENTION

The present disclosure provides a process for the preparation of a compound of Formula II, Formula II

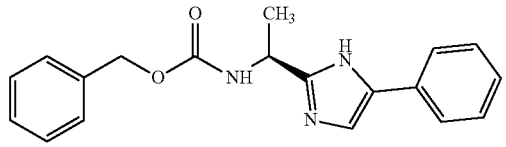

comprising cyclizing $N^2$-[(benzyloxy)carbonyl]-N-(2-oxo-2-phenylethyl)-L-alaninamide of Formula III in the presence of ammonium acetate and toluene, Formula III

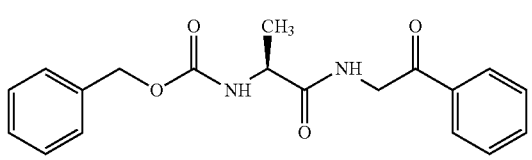

wherein the molar ratio of ammonium acetate to $N^2$-[(benzyloxy)carbonyl]-N-(2-oxo-2-phenylethyl)-L-alaninamide of Formula III is from 6:1 to 9:1, and then removing water produced during the cyclizing by azeotropic distillation.

In some embodiments, the compound of Formula II is further converted to eluxadonline (Formula I)

Formula I

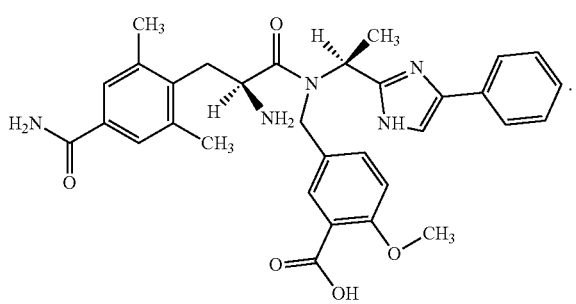

In some embodiments, the cyclization of $N^2$-[(benzyloxy)carbonyl]-N-(2-oxo-2-phenylethyl)-L-alaninamide of Formula III to obtain the compound of Formula II is carried out in the presence of acetic acid. In some embodiments, the acetic acid and the toluene are mixed together prior to being added to the $N^2$-[(benzyloxy)carbonyl]-N-(2-oxo-2-phenylethyl)-L-alaninamide and toluene. In some embodiments, the acetic acid and the toluene are in a ratio of about 1:3 to about 1:8 (vol/vol). In some embodiments, the acetic acid and the toluene are in a ratio of about 1:4 to about 1:6 (vol/vol). In some embodiments, the cyclization of $N^2$-[(benzyloxy)carbonyl]-N-(2-oxo-2-phenylethyl)-L-alaninamide of Formula III is conducted at a temperature of about 80° C. to about 140° C. In some embodiments, the cyclization of $N^2$-[(benzyloxy)carbonyl]-N-(2-oxo-2-phenylethyl)-L-alaninamide of Formula III is conducted at a temperature of about 100° C. to about 120° C. In some embodiments, the cyclization of $N^2$-[(benzyloxy)carbonyl]-N-(2-oxo-2-phenylethyl)-L-alaninamide of Formula III proceeds for 2 to 8 hours. In some embodiments, the cyclization of $N^2$-[(benzyloxy)carbonyl]-N-(2-oxo-2-phenylethyl)-L-alaninamide of Formula III proceeds for 3 to 5 hours.

In some embodiments, after the water is removed azeotropically, the resulting product of the cyclization, the compound of Formula 2, is further purified using a mixture of solvents with different polarities at a basic pH. In some embodiments, the mixture of solvents comprises a solvent selected from the group consisting of water, ethyl acetate, methanol, or combinations thereof. In some embodiments, after the water is removed azeotropically, the resulting product of the cyclization is precipitated using a benzene derivative. In some embodiments, the benzene derivative is toluene. In some embodiments, the process provides a compound of Formula II at greater than 90% chromatographic purity without the use of column chromatography. In some embodiments, the process provides a compound of Formula II at greater than 95% chromatographic purity without the use of column chromatography.

In some embodiments, the disclosure provides a process for the preparation of eluxadoline of Formula I, Formula I

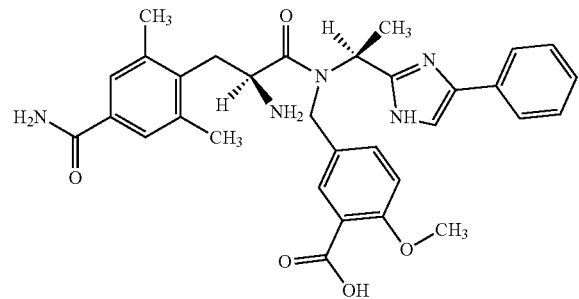

comprising (a) cyclizing N²-[(benzyloxy)carbonyl]-N-(2-oxo-2-phenylethyl)-L-alaninamide of Formula III in the presence of ammonium acetate and toluene Formula III

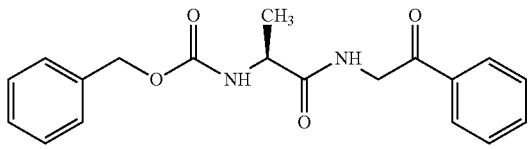

to obtain a compound of Formula II,

Formula II

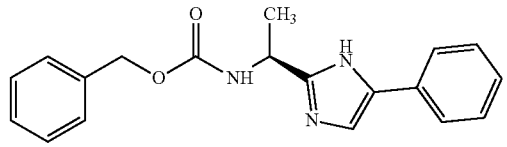

wherein the molar ratio of ammonium acetate to N²-[(benzyloxy)carbonyl]-N-(2-oxo-2-phenylethyl)-L-alaninamide of Formula III is from 6:1 to 9:1, then removing water produced by the cyclizing by azeotropic distillation; and (b) converting the compound of Formula II to eluxadoline of Formula I.

In some embodiments, the disclosure provides a process for the preparation of a compound of Formula II, Formula II

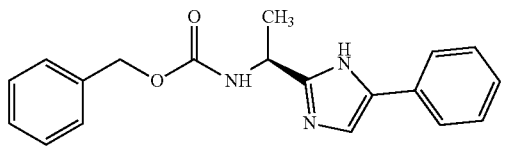

comprising (a) cyclizing N²-[(benzyloxy)carbonyl]-N-(2-oxo-2-phenylethyl)-L-alaninamide of Formula III in the presence of ammonium acetate and toluene, Formula III

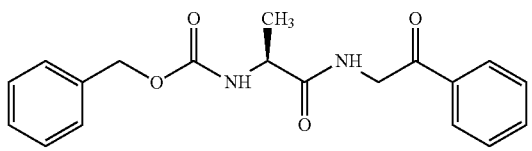

wherein the molar ratio of ammonium acetate to N²-[(benzyloxy)carbonyl]-N-(2-oxo-2-phenylethyl)-L-alaninamide of Formula III is from 6:1 to 9:1, (b) removing water produced during the cyclizing by azeotropic distillation; (c) purifying the product of (b) using a mixture of solvents with different polarities at a basic pH; and (d) precipitating the product of (c) using a benzene derivative.

DETAILED DESCRIPTION OF THE INVENTION

The present disclosure relates to processes for the preparation of eluxadoline and its intermediates. The present disclosure provides an environmentally friendly, cost-effective, and industrially advantageous process for the preparation of eluxadoline and its intermediates. The process of the present disclosure provides the compound of Formula II in high purity. In some embodiments, the process of the present disclosure provides a method of producing the compound of Formula II at high purity without the use of column chromatography. In some embodiments, the process of the present disclosure provides a method of producing the compound of Formula II more quickly relative to the methods found in U.S. Pat. No. 7,741,356, since column chromatography may not be necessary.

The term "about," as used herein, refers to any value which lies within the range defined by a number up to ±10% of the value.

The term "room temperature," as used herein, refers to a temperature in the range of 25° C. to 35° C.

In some embodiments, the present disclosure provides a process for the preparation of a compound of Formula II, Formula II

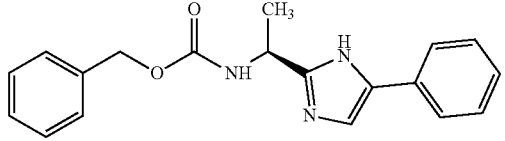

comprising cyclizing N²-[(benzyloxy)carbonyl]-N-(2-oxo-2-phenylethyl)-L-alaninamide of Formula III in the presence of ammonium acetate and toluene, Formula III

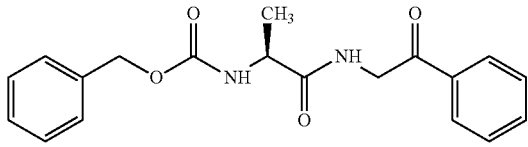

wherein the molar ratio of ammonium acetate to N²-[(benzyloxy)carbonyl]-N-(2-oxo-2-phenylethyl)-L-alaninamide of Formula III is from 6:1 to 9:1, and then removing water produced during cyclization by azeotropic distillation. In some embodiments, the compound of Formula II is further converted to eluxadonline (Formula I)

Formula I

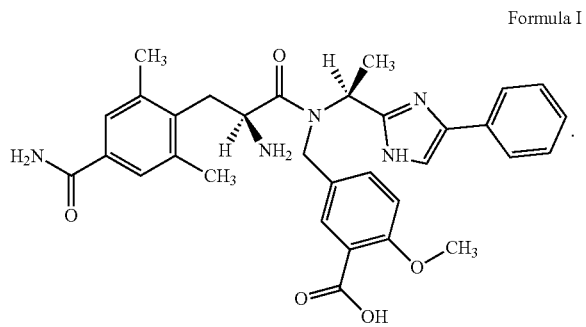 [SMILES: COc1ccc(CN(C(=O)[C@@H](N)Cc2c(C)cc(C(N)=O)cc2C)[C@@H](C)c2nc(-c3ccccc3)c[nH]2)cc1C(=O)O]

In some embodiments, the disclosure provides a process of the preparation of eluxadoline of Formula I, Formula I

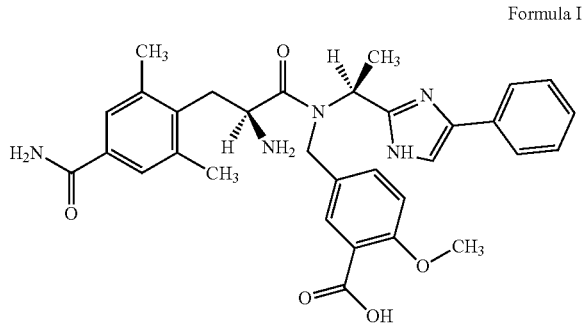 [SMILES: COc1ccc(CN(C(=O)[C@@H](N)Cc2c(C)cc(C(N)=O)cc2C)[C@@H](C)c2nc(-c3ccccc3)c[nH]2)cc1C(=O)O]

comprising (a) cyclizing N²-[(benzyloxy)carbonyl]-N-(2-oxo-2-phenylethyl)-L-alaninamide of Formula III in the presence of ammonium acetate and toluene Formula III

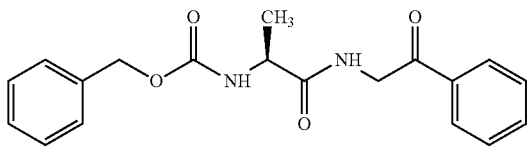

to obtain a compound of Formula II,

Formula II

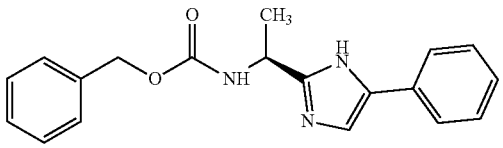

wherein the molar ratio of ammonium acetate to N²-[(benzyloxy)carbonyl]-N-(2-oxo-2-phenylethyl)-L-alaninamide of Formula III is from 6:1 to 9:1, then removing the water of the reaction by azeotropic distillation; and (b) converting the compound of Formula II to eluxadoline of Formula I.

N²-[(Benzyloxy)carbonyl]-N-(2-oxo-2-phenylethyl)-L-alaninamide of Formula III may be prepared by any method known in the art, for example, the method described in U.S. Pat. No. 7,741,356.

In some embodiments, the disclosure provides efficient, cost-sensitive, time-sensitive, and environmentally sensitive methods of converting N²-[(benzyloxy)carbonyl]-N-(2-oxo-2-phenylethyl)-L-alaninamide of Formula III to the compound of Formula II. In some embodiments, the highly purified compound of Formula II produced by the present disclosure can be further reacted to produce the compound of Formula I. By provide a more efficient method of producing this intermediate, the compound of Formula I can also be produced more efficiently. Thus, the present invention also provides a method of producing the compound of Formula I.

In some embodiments, the cyclization of N²-[(benzyloxy)carbonyl]-N-(2-oxo-2-phenylethyl)-L-alaninamide of Formula III to obtain the compound of Formula II as described herein is carried out in the presence of acetic acid. Thus, for example, in some embodiments, the cyclization reaction would involve N²-[(benzyloxy)carbonyl]-N-(2-oxo-2-phenylethyl)-L-alaninamide, acetic acid, toluene and ammonium acetate. In some embodiments, the acetic acid and the toluene are mixed together prior to being added to the N²-[(benzyloxy)carbonyl]-N-(2-oxo-2-phenylethyl)-L-alaninamide and toluene. In some embodiments, the acetic acid and the toluene are mixed together at a temperature of 30° C. to about 55° C., or about 40° C. to about 45° C. In some embodiments, the acetic acid and the toluene are in a ratio of about 1:3 to about 1:8 (vol/vol), or in a ratio of about 1:4 to about 1:6 (vol/vol), or about 1:5.

Various ratios of toluene to the compound of Formula III can be used during the cyclization reaction, e.g., in some embodiments, about 200 ml to about 5 L of toluene can added to about 100 g the compound of Formula III, or about 500 ml to about 2 L of toluene can added to about 100 g the compound of Formula III. In some embodiments, a ratio of about 800 ml to about 1.5 L of toluene, or about 1 L of toluene can be added to about 100 g of the compound of Formula III.

In some embodiments, various ratios of acetic acid to the compound of Formula III can be used during the cyclization reaction, e.g., in some embodiments, about 20 ml to about 1 L of acetic acid can added to about 100 g the compound of Formula III, or about 50 ml to about 500 ml of acetic acid can added to about 100 g the compound of Formula III. In some embodiments, a ratio of about 100 ml to about 300 ml of acetic acid, or about 200 ml of acetic acid can be added to about 100 g of the compound of Formula III.

The cyclization of N²-[(benzyloxy)carbonyl]-N-(2-oxo-2-phenylethyl)-L-alaninamide of Formula III can be carried out for about 30 minutes to about 10 hours, for example, for about 1 hour to about 9 hours, about 2 hours to about 8 hours, or about 3 hours to about 5 hours. In some embodiments, the cyclization of N²-[(benzyloxy)carbonyl]-N-(2-oxo-2-phenylethyl)-L-alaninamide of Formula III can be carried out for about 4 hours.

The cyclization of N²-[(benzyloxy)carbonyl]-N-(2-oxo-2-phenylethyl)-L-alaninamide of Formula III is carried out at a temperature of from about 80° C. to about 140° C., for example, from about 100° C. to about 120° C., or from about 105° C. to about 110° C.

The compound of Formula II may optionally be isolated or further purified by filtration, decantation, extraction, distillation, evaporation, chromatography, precipitation, concentration, crystallization, centrifugation, or recrystallization. In some embodiments, the compound of Formula II is isolated without using chromatography, e.g., without using column chromatography.

In some embodiments, after the water is removed azeotropically as described herein, the resulting product of the cyclization, the compound of Formula II, is further purified using a mixture of solvents with different polarities at a basic pH. In some embodiments, the product resulting from cyclization is mixed with a basic solvent, e.g., water, ethyl acetate, methanol, or combinations thereof with a pH of greater than 8, greater than 9 or greater than 10. In some embodiments, the basic solvent has a pH of about 9.5 to about 10.5, or about 10.0. The mixture of the product from the cyclization and the basic solvent can then be mixed, e.g., at room temperature. The layers of the resulting product can then be separated, with the aqueous layer optionally be extracted with toluene. In some embodiments, the mixture of solvents comprises a solvent selected from the group consisting of water, ethyl acetate, methanol, or combinations thereof. In some embodiments, after the water is removed azeotropically, the resulting product of the cyclization is precipitated using a benzene derivative, e.g., toluene.

The processes provided herein provide a process for preparing the compound of Formula II, wherein the compound of Formula II is prepare at greater than 90% chromatographic purity without the use of column chromatography. In some embodiments, Formula II is prepared at greater than 95% chromatographic purity without the use of column chromatography. The term "chromatographic purity" as used herein refers to a standard chromatographic method for determining purity. In some embodiments, "chromatographic purity" refers to purity as determined by HPLC. In some embodiments, "chromatographic purity" refers to purity as determined by TLC.

The compound of Formula II may be dried using conventional techniques, for example, drying, drying under vacuum, suck drying, spray drying, air drying, or agitated thin film drying.

The compound of Formula II is converted to eluxadoline of Formula I by processes known in the art, for example, as disclosed in U.S. Pat. No. 7,741,356. In some embodiments, the disclosure provides a process for the preparation of a compound of Formula II,

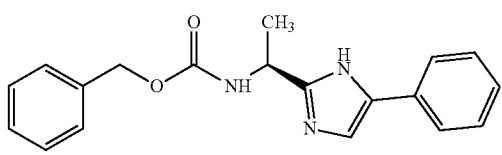

Formula II comprising (a) cyclizing N-[(benzyloxy)carbonyl]-N-(2-oxo-2-phenylethyl)-L-alaninamide of Formula III in the presence of ammonium acetate and toluene,

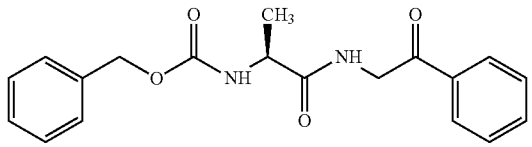

Formula III wherein the molar ratio of ammonium acetate to N²-[(benzyloxy)carbonyl]-N-(2-oxo-2-phenylethyl)-L-alaninamide of Formula III is from 6:1 to 9:1, (b) removing water produced during the cyclizing by azeotropic distillation; (c) purifying the product of (b) using a mixture of solvents with different polarities at a basic pH; and (d) precipitating the product of (c) using a benzene derivative.

While the present invention has been described in terms of its specific aspects and embodiments, certain modifications and equivalents will be apparent to those skilled in the art, and are intended to be included within the scope of the present invention.

Method

Chromatographic purity was determined using a Waters® Acquity® UPLC, H-Class System, Model ChA. The column used was an Acquity® HSS C-18 (100×2.1 mm) 1.8 m.

The following examples are for illustrative purposes only and should not be construed as limiting the scope of the invention in any way.

EXAMPLES

Example 1: Preparation of benzyl [(1S)-1-(5-phenyl-1H-imidazol-2-yl)ethyl]carbamate (Formula II) as Per Procedure Disclosed in U.S. Pat. No. 7,741,356

N²-[(Benzyloxy)carbonyl]-N-(2-oxo-2-phenylethyl)-L-alaninamide (10 g, Formula III) in xylene (230 mL) was added to a mixture of ammonium acetate (39.6 g) and acetic acid (19.2 mL) at room temperature. The reaction mixture was heated to reflux temperature and then stirred for 7 hours. The reaction mixture was cooled to room temperature, and then a brine solution (100 mL, 10 T) was added. The mixture was stirred for 10 minutes, and then the layers were separated. The organic layer was washed with brine solution (100 mL). The separated brine layer was again extracted with ethyl acetate (50 mL). The combined organic layers were recovered completely at 60° C. to obtain a residue. The residue was purified by column chromatography on silica gel (ethyl acetate:hexane 1:1) to obtain the title compound.

Yield: 8.77 g
Chromatographic Purity: 83.4%

Example 2: Preparation of benzyl [(1S)-1-(5-phenyl-1H-imidazol-2-yl)ethyl]carbamate (Formula II)

Method A:

Toluene (1 L) and acetic acid (200 mL) were combined and then heated to 40° C. to 45° C. Ammonium acetate (158.4 g) and N²-[(benzyloxy)carbonyl]-N-(2-oxo-2-phenylethyl)-L-alaninamide (100 g, Formula III) were added to the mixture at 40° C. to 45° C. The reaction mixture was then heated to 105° C. to 110° C., and then the water was removed azeotropically using a Dean-Stark apparatus. The mixture was cooled to room temperature, and then water (1 L) was added. Sodium hydroxide (20%, ~800 mL) was added to the reaction mixture to adjust the pH to 12.52, and then the mixture was stirred for 10 minutes at 40° C. to 45° C. The layers were separated, and then the aqueous layer was extracted with toluene (500 mL). The combined organic layers were recovered up to 250 mL, then cooled to 10° C. to 15° C., and then stirred for 30 minutes. The solid so obtained was filtered, and then washed with toluene (50 mL) at 10° C. to 15° C. The solid was dried overnight under an air oven at 50° C. to 55° C. to obtain the title compound.

Yield: 77.45 g

Chromatographic purity: 98.5%

Method B:

Toluene (500 mL) and acetic acid (100 mL) were combined and then heated to 40° C. to 45° C. to obtain a mixture. Ammonium acetate (80 g) and $N^2$-[(benzyloxy)carbonyl]-N-(2-oxo-2-phenylethyl)-L-alaninamide (50 g, Formula III) were added to the mixture, and then the mixture was heated to 105° C. to 110° C. Water was removed azeotropically using a Dean-Stark apparatus. The reaction mixture was refluxed for 4 hours, and then cooled to room temperature. Ethyl acetate (250 mL) and water (500 mL) were added to the mixture, and then the pH of the mixture was adjusted to 12.02 using a sodium hydroxide solution (30%, ~150 ml). The layers were separated, and then the aqueous layer was extracted with ethyl acetate (250 mL). The combined organic layers were recovered completely, and then toluene (250 mL) was added. The mixture was heated to 55° C. to 60° C. The solvent was recovered up to 100 mL, and then the mixture was cooled to 25° C. to 30° C. The mixture was stirred for 30 minutes to 40 minutes at 25° C. to 30° C. to obtain a solid. The solid so obtained was filtered, then washed with toluene (100 mL), then suck dried, and then dried overnight under vacuum at 50° C. to 55° C. to obtain the title compound.

Yield 38.9 g

Chromatographic purity: 96.98%

Method C:

Toluene (500 mL) and acetic acid (100 mL) were combined and then heated to 40° C. to 45° C. to obtain a mixture. Ammonium acetate (80 g) and $N^2$-[(benzyloxy)carbonyl]-N-(2-oxo-2-phenylethyl)-L-alaninamide (50 g, Formula III) were added to the mixture, and then the mixture was heated to 105° C. to 110° C. Water was removed azeotropically using a Dean-Stark apparatus. The reaction mixture was refluxed for 4 hours, and then cooled to room temperature. Methanol (175 mL) and water (250 mL) were added to the mixture, and then the pH of the mixture was adjusted to 12.2 using a sodium hydroxide solution (30%, ~150 ml). The layers were separated, and then the aqueous layer was extracted with toluene (250 mL). The combined organic layers were recovered up to 100 mL, and then cooled to 25° C. to 30° C. The mixture was stirred for 30 minutes at 25° C. to 30° C. The solid so obtained was filtered, then washed with chilled toluene (100 mL), then suck dried, and then dried overnight under vacuum at 50° C. to 55° C. to obtain the title compound.

Yield: 32.8 g

Chromatographic purity: 99.72%

The invention claimed is:

1. A process for the preparation of a compound of Formula II,

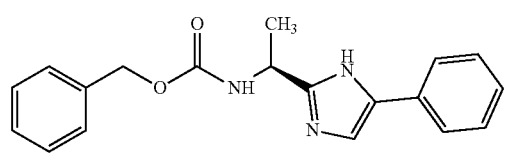

Formula II comprising cyclizing $N^2$-[(benzyloxy)carbonyl]-N-(2-oxo-2-phenylethyl)-L-alaninamide of Formula III in the presence of ammonium acetate and toluene,

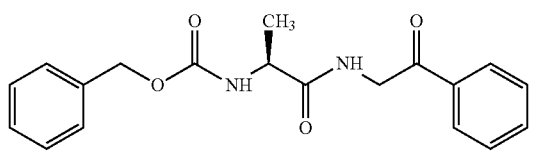

Formula III wherein the molar ratio of ammonium acetate to $N^2$-[(benzyloxy)carbonyl]-N-(2-oxo-2-phenylethyl)-L-alaninamide of Formula III is from 6:1 to 9:1.

2. The process according to claim 1, wherein the cyclization of $N^2$-[(benzyloxy)carbonyl]-N-(2-oxo-2-phenylethyl)-L-alaninamide of Formula III to obtain the compound of Formula II is carried out in the presence of acetic acid.

3. The process of claim 2, wherein the cyclization of $N^2$-[(benzyloxy)carbonyl]-N-(2-oxo-2-phenylethyl)-L-alaninamide of Formula III is carried out in the presence of acetic acid and the toluene in a ratio of about 1:3 to about 1:8 (vol/vol).

4. The process according to claim 2, wherein the cyclization of $N^2$-[(benzyloxy)carbonyl]-N-(2-oxo-2-phenylethyl)-L-alaninamide of Formula III is conducted at a temperature of about 80° C. to about 140° C.

5. The process according to claim 2, wherein the cyclization of $N^2$-[(benzyloxy)carbonyl]-N-(2-oxo-2-phenylethyl)-L-alaninamide of Formula III proceeds for 2 to 8 hours.

6. The process according to claim 1, wherein the compound of Formula II is further converted to eluxadoline of Formula I

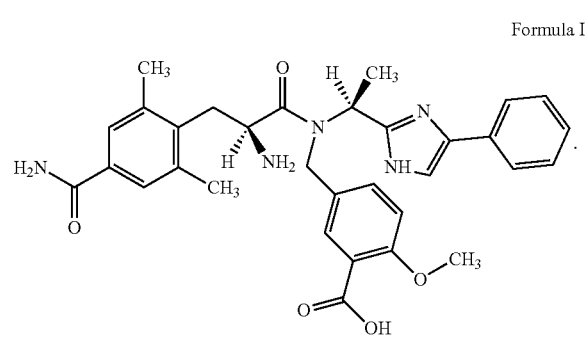 [SMILES: COc1ccc(CN(C(=O)[C@@H](N)Cc2c(C)cc(C(N)=O)cc2C)[C@@H](C)c2nc(-c3ccccc3)c[nH]2)cc1C(=O)O]

Formula I

* * * * *